(12) United States Patent
Granov et al.

(10) Patent No.: US 8,306,611 B2
(45) Date of Patent: Nov. 6, 2012

(54) METHOD AND SYSTEM FOR USE IN MONITORING LEFT VENTRICULAR DYSFUNCTION

(75) Inventors: Evgeny Granov, Ra'anana (IL); Igor Granov, Raanana (IL); Daniel A. Goor, Tel Aviv (IL); Efim Frinerman, Bat Yam (IL)

(73) Assignee: N.I Medical Ltd., Kfar Malal (IL)

( * ) Notice: Subject to any disclaimer, the term of this patent is extended or adjusted under 35 U.S.C. 154(b) by 0 days.

(21) Appl. No.: 12/855,362

(22) Filed: Aug. 12, 2010

(65) Prior Publication Data

US 2011/0034815 A1 Feb. 10, 2011

Related U.S. Application Data

(63) Continuation of application No. PCT/IL2009/000173, filed on Feb. 12, 2009.

(60) Provisional application No. 61/064,062, filed on Feb. 14, 2008.

(51) Int. Cl.
*A61B 5/04* (2006.01)

(52) U.S. Cl. ...................................... 600/509

(58) Field of Classification Search .................. 600/509
See application file for complete search history.

(56) References Cited

U.S. PATENT DOCUMENTS

| | | | |
|---|---|---|---|
| 5,330,513 A * | 7/1994 | Nichols et al. | 607/32 |
| 5,469,859 A | 11/1995 | Tsoglin et al. | |
| 5,735,284 A | 4/1998 | Tsoglin et al. | |
| 6,038,476 A | 3/2000 | Schwartz | |
| 6,161,038 A * | 12/2000 | Schookin et al. | 600/519 |
| 2008/0009759 A1 | 1/2008 | Chetham | |

FOREIGN PATENT DOCUMENTS

| | | |
|---|---|---|
| WO | 9724984 A1 | 7/1997 |
| WO | 02078539 A1 | 10/2002 |

OTHER PUBLICATIONS

Thomas J. Wang, MD et al. The Epidemiology of "Asymptomatic" Left Ventricular Systolic Dysfunction: Implications for Screening, published in Annals of Internal Medicine, Jun. 3, 2003, vol. 138, No. 11, pp. 907-916.
Kevin C. Allman, MB, BS et al. Myocardial Viability Testing and Impact of Revascularization on Prognosis in Patients With Coronary Artery Disease and Left Ventricular Dysfunction: A Meta-Analysis, published in Journal of the American College of Cardiology in vol. 39, No. 7, 2002, pp. 1151-1159.
Thomas J. Wang et al. Natural History of Asymptomatic Left Ventricular Systolic Dysfunction in the Community, published in Circulation, Journal of the American Heart Association, Aug. 26, 2003 pp. 977-982.
International Search Report, mailed Jun. 9, 2009, from International Application No. PCT/IL 09/00173.

* cited by examiner

*Primary Examiner* — George Manuel
(74) *Attorney, Agent, or Firm* — Patentbar International, P.C.

(57) ABSTRACT

A method and system are presented for use in determining a patient's heart condition. First and second data are provided, where the first data is indicative of the patient's heart rate, and the second data is indicative of bioimpedance peak value during a cardiac cycle. A relation between a certain predetermined value and a product of the first and said second data is determined, where such relation is indicative of the patient's left ventricular condition, enabling to identify a left ventricular dysfunction.

19 Claims, 3 Drawing Sheets

METHOD AND SYSTEM FOR USE IN MONITORING LEFT VENTRICULAR DYSFUNCTION

RELATED APPLICATIONS

This application is a Continuation of International Application No. PCT/IL2009/000173 filed Feb. 12, 2009, which claims priority to U.S. Provisional Application No. 61/064,062 filed Feb. 14, 2008.

FIELD OF THE INVENTION

The present invention is generally in the field of bioimpedance based monitoring techniques, and relates to a method and system for monitoring a patient's condition aimed at determining left ventricular dysfunction.

BACKGROUND OF THE INVENTION

Congestive heart failure (CHF) is most commonly associated with dilated left ventricle (LV) and/or its systolic dysfunction which is characterized by decreased ejection fraction (EF). In particular, a less 55% ejection fraction (EF) is the cut-off point for LV dysfunction (Wang T J, Levy D, Benjamin E J, Vasan R S. The Epidemiology of "Asymptomatic" left ventricular systolic dysfunction: Implications for screening. Ann Intern Med 2003; 138:907-913).

Regardless of its etiology, asymptomatic left ventricular systolic dysfunction (ALVSD) is considered an independent clinical entity as long as it is asymptomatic. Because of its progressive nature, when the ejection fraction (EF) declines below the 40% level, clinical signs, particularly of CHF, enable diagnosis and therapy. Hence it is the covert phase of 55%>EF>40% which remains undiagnosed, and which is prone to deteriorate either into an advanced stage of CHF, or to sudden cardiac death. On the one hand, CHF is considered one of the greatest medical economic burdens in the Western world, and early detection with the appropriate relative medical therapy would significantly improve the outlook of these patients. On the other hand, the largest population of patients with the ALVSD condition consists of individuals who have unrecognized coronary heart disease (CHD), including hibernating myocardium. The annual mortality, for example, of fatal arrhythmias in untreated hibernating myocardium is 16% (Allman K C, Shaw L J, Hachamovitch R, Udelson J E. "Myocardial viability testing and impact of revascularization on prognosis in patients with coronary artery disease and left ventricular dysfunction: a meta-analysis.", J Am Coll Cardiol 2002; 39:1151-1158).

As the incidence of ALVSD in the community ranges from 3-7.7% (Wang T J, Evans J C, Benjamin E J, Levy D, LeRoy E C, Vasan R S., "Natural history of asymptomatic left-ventricular systolic dysfunction in the community", Circulation 2003; 108:977-982), the only effective way to reduce the risks of ALVSD would be by diagnostic screening of the community (Wang T J, Levy D, Benjamin E J, Vasan R S., "The Epidemiology of "Asymptomatic" left ventricular systolic dysfunction: Implications for screening", Ann Intern Med 2003; 138:907-913).

Techniques for non-invasive measuring and monitoring various hemodynamic parameters of a patient, such as cardiac parameters, utilizing body bioimpedance techniques have been developed. Some of such techniques are disclosed for example in the following patent publications: WO 02/078539, WO 97/24984, U.S. Pat. Nos. 5,469,859, 5,735,284, all assigned to the assignee of the present application.

SUMMARY OF THE INVENTION

There is a need in the art to facilitate early diagnostics of the left-ventricular (LV) dysfunction. The technologies available for diagnosing LV dysfunction (EF<55%), like echo-cardiography, radionuclide ventriculography, and cardiac catheterization, are too expensive, and therefore impractical for screening ALVD.

The present invention provides a novel technique for simple and precise monitoring of the patient's condition enabling early diagnostics of the LV dysfunction. The invented technique utilizes bioimpedance measurements, namely measurement of a basic signal $\Delta R/R$ (or $\Delta Z/Z$) where $\Delta R$ or $\Delta Z$ is the peripherally depicted signal which is a reliable signal in representing the original source of the pure resistance change or impedance change, and multiplies the $\Delta R/R$ or $\Delta Z/Zo$ parameter by a systolic peak time parameter ($\alpha$)

The inventors have found that a product of a first data, indicative of the patient's heart rate, and a second data, indicative of bioimpedance variations during the systolic peak time of the patient's cardiac cycle, can be related to a certain predetermined value, and this relation is indicative of the left ventricular function. The predetermined value, discovered by the inventors and termed "Granov-Goor index" or "GGI", appears to be a threshold defining a boundary between the healthy and diseased conditions with respect to the left ventricular function.

In some embodiments of the invention, the first data indicative of the patient's heart rate comprises a patient's heart rate value. Preferably, however, this first data indicative of the patient's heart rate comprises a product of the patient's heart rate value and a certain coefficient $k_{HR}$. The latter is specific for a patient, and presents a correction coefficient for correction of $\alpha$, which is the systolic peak time of a cardiac cycle. This correction coefficient $k_{HR}$ is determined as follows:

it is equal to 1 when the measured patient's heart rate $HR_{meas}$ is within a certain range of normal values between a bottom limit BL and a top limit TL (which range is 60-90 according to the existing standards);

it is equal to $BL/HR_{meas}$ when the measured patient's heart rate $HR_{meas}$ is less than the bottom limit BL of the normal range; and it is equal to $TL/HR_{meas}$ when the heart rate $HR_{meas}$ is higher than the top limit TL of the normal range.

As for the second data, indicative of electrical bioimpedance changes during the systolic peak time of cardiac cycle, it in some embodiments of the invention is defined as a product of a normalized systolic impedance variation, $\Delta R/R$, and the systolic peak time.

Thus, considering the first data to be $(HR_{meas} \cdot k_{HR})$ and the second data to be $$\left(\frac{\Delta R}{R} \cdot \alpha\right),$$

the certain predetermined value, being a threshold defining a boundary between the healthy and diseased conditions with respect to the left ventricular function, is equal to 10. In other words, a relation $$\frac{\Delta R}{R} \cdot \alpha \cdot HR \cdot k_{HR} < 10$$

corresponds to a condition of the left-ventricular dysfunction, and a relation $$\frac{\Delta R}{R} \cdot \alpha \cdot HR \cdot k_{HR} \geq 10$$

corresponds to a healthy condition with this respect. It should be noted that, in order to provide well correlation of the measurement technique of the present invention with the common function assessment tools, the range of measured values for $$\frac{\Delta R}{R} \cdot \alpha \cdot HR \cdot k_{HR}$$

is limited to a certain number, let's say 12, beyond which there is no diagnostic meaning.

Thus, according to one broad aspect of the invention, there is provided a method for determining a patient's heart condition, the method comprising:
  providing first data indicative of the patient's heart rate;
  providing second data indicative of bioimpedance peak value during a cardiac cycle;
  determining a relation between a product of said first and said second data and a certain predetermined value, said relation being indicative of the patient's left ventricular condition enabling to identify left ventricular dysfunction.

According to another broad aspect of the invention, there is provided a system for use in determining a patient's heart condition, the system comprising:
  a data input utility for receiving first data indicative of the patient's heart rate and receiving second data indicative of bioimpedance peak value during a cardiac cycle;
  a data processing and analyzing utility configured for determining a product of said first and said second data, determining a relation between said product and a certain predetermined value, and based on said relation generating data indicative of the patient's left ventricular condition; and
  a data output utility for exposing to user data indicative of the patient's left ventricular condition.

The data input utility may be responsive to user entered data comprising at least one of said first and second data, and/or responsive to output data of a measurement device comprising at least one of said first and second data. In the latter case, the data input utility comprises an appropriate communication unit for connecting to measurement device(s), via wires or wireless signal transmission.

The above-described system is typically a computer system, which may include any other hardware/software, such as memory, data presentation (e.g. display), etc.

The data processing and analyzing utility is configured and operable (programmed) to receive the first and second input data and process them to determine whether the product of said first and said second data satisfies a predetermined condition (namely whether the product of said first and said second data is less than said certain predetermined value) and, if so, generating data indicative of whether the condition of the patient's left ventricular dysfunction exists or not. It should be understood that the data processing and analyzing utility may calculate the first and second data based on, respectively, the input measured heart rate, and the measured values of $\Delta R/R$ or $\Delta Z/Z_o$ and $\alpha$.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
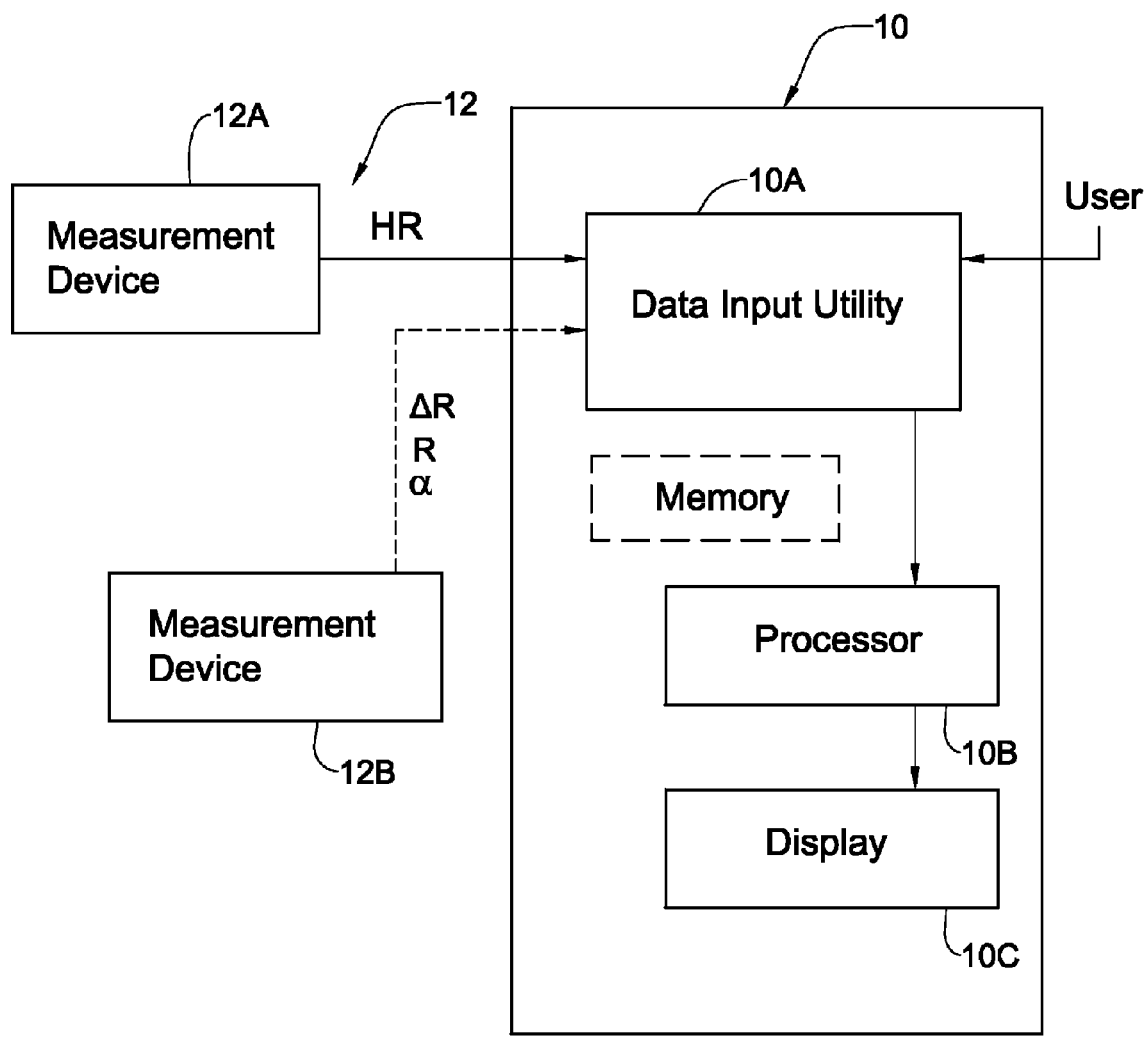
FIG. 1 is a schematic illustration of a system according to the invention for use in determining a patient's heart condition.

Referring to FIG. 1, there is illustrated, by way of a block diagram, a monitoring system 10 according to the invention. The system 10 is configured and operable for determining a patient's heart condition. The system 10 is typically a computer system including inter alia a data input utility 10A, a data processing and analyzing utility 10B, a data output utility 10C (e.g. display).

Figure 3:
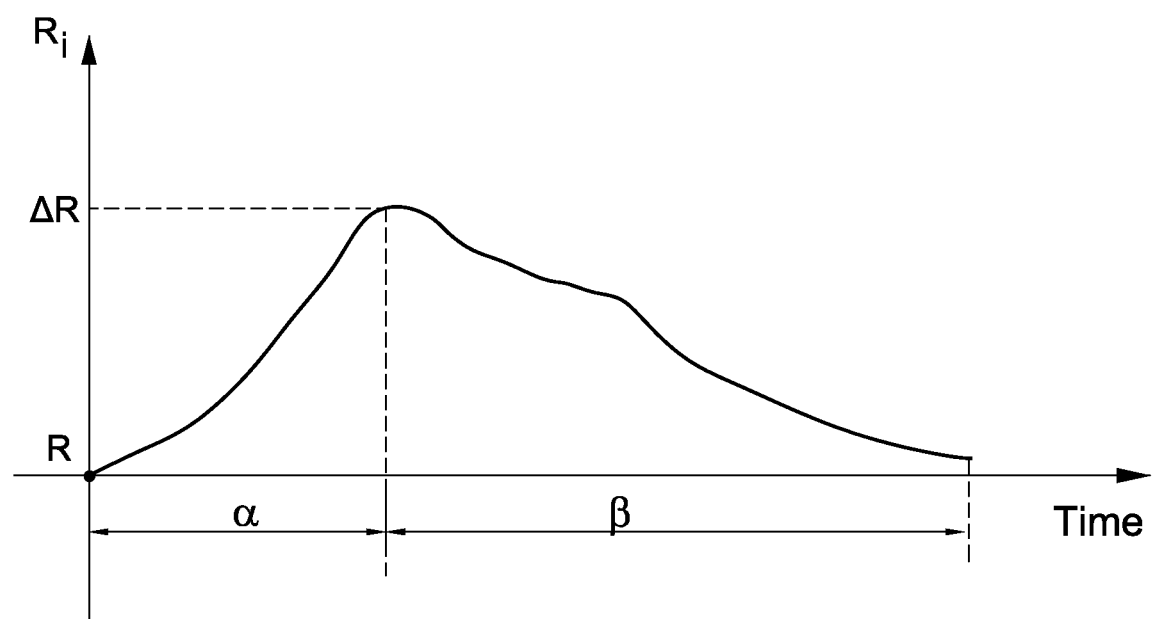
FIG. 3 illustrates the bioimpedance peak systolic value and a during a cardiac cycle.

The data input utility is configured for receiving data indicative of the patient's heart rate (constituting first data) and for receiving data indicative of bioimpedance variations during a cardiac cycle (constituting second data). The data input utility may include keyboard or the like for entering user data, and/or may include an appropriate communication utility (not shown) for connecting (via wires or wireless) to external measurement device(s) 12, and/or for connecting to external database. In the present specific but not limiting example, the system connection to two measurement devices 12A and 12B is shown, for receiving the first and second data respectively. In the present example, the first input data piece includes the patient's heart rate value, and the second input data piece includes data indicative of bioimpedance variations during a cardiac cycle. Such bioimpedance variations during a cardiac cycle are illustrated in FIG. 3, showing the bioimpedance change $\Delta R$ relative to the base value R during the cardiac cycle. The cardiac cycle includes an ejection time ET interval and the remaining diastola. It should be understood that the second data coming from the measurement device actually includes results of one or more measurement sessions, each including more than one cardiac cycle.

The data processing and analyzing utility 10B is preprogrammed for calculating a product of the first and said second data, and determining a relation between this product and a certain predetermined value. The determined relation is indicative of the patient's left ventricular condition. The processing results are then exposed (e.g. displayed) to user. More specifically, the data processing and analyzing utility operates to determine whether said product of the first and said second data is less than said certain predetermined value, and if so generating data indicative of the condition of the patient's left ventricular dysfunction.

In some embodiments of the invention, the data processing and analyzing utility receives the measured heart rate value and defines a correction coefficient $k_{HR}$ as follows:

$k_{HR}=1$ if $HR_{meas}$ is within a certain range of normal values between a bottom limit BL (e.g. 60) and a top limit TL (e.g. 90);

$k_{HR}=BL/HR_{meas}$ when $HR_{meas}<BL$, and $k_{HR}=TL/HR_{meas}$ when $HR_{meas}>TL$.

Then, the first data is determined as $(HR \cdot k_{HR})$.

Independently, the data processor and analyzing utility operates to receive the respective measured data and determine the second data as a product $(\Delta R/R \cdot \alpha)$.

Then, the data processing and analyzing utility operates to determine a product between the first and second data, $(HR \cdot k_{HR} \cdot \Delta R/R \cdot \alpha)$.

Thereafter, the above product is analyzed with respect to a predetermined threshold value, which as found by the inventors is being equal to 10.

The physical meaning of the product $(HR \cdot k_{HR} \cdot \Delta R/R \cdot \alpha)$ is associated with the following: As can be understood from the illustration in FIG. 3, the value $(\frac{1}{2}(HR \cdot k_{HR} \cdot \Delta R/R \cdot \alpha))$ actually characterizes the blood volume ejected during the peak systolic time of the cardiac cycle, thus characterizing the condition of the left ventricular activity of the patient, because the left ventricular operation is dominant during the peak systolic time of the cardiac cycle.

Figure 2:
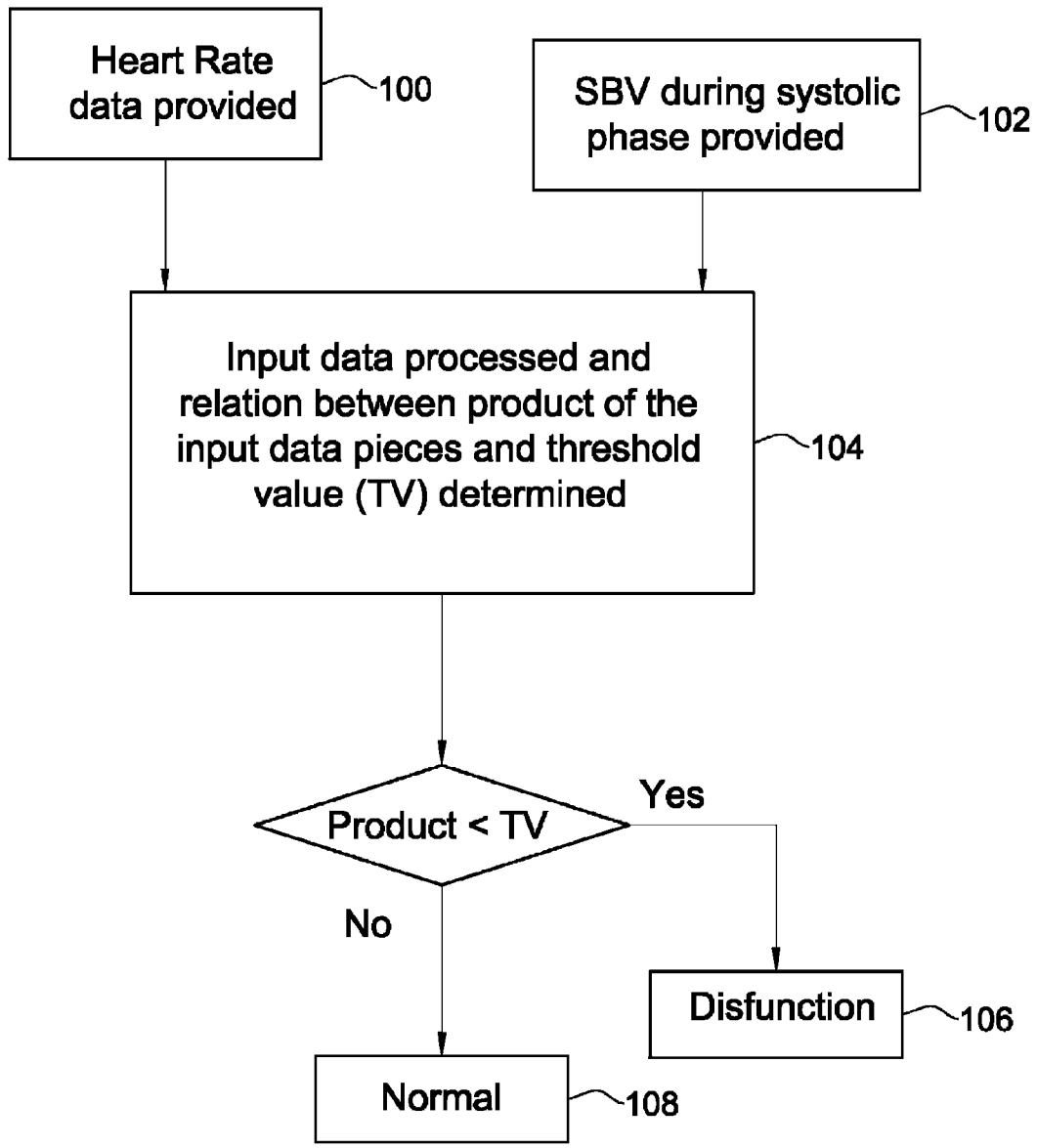
FIG. 2 is a flow chart of an example of a method according to the invention for use in determining a patient's heart condition.

Reference is made to FIG. 2 exemplifying a method according to the invention for determining the patient's left ventricular condition. As shown, the heart rate data (first data) and bioimpedance systolic peak value (SPV) during the cardiac cycle (second data) are independently provided (step 100) and (step 102). These data pieces are processed to calculate the product thereof and determine a relation between this product and a certain threshold value (TV), e.g. 10 (step 104). If the product value is less than TV, then the patient's heart condition is considered as having left ventricular dysfunction (step 106) and if the product is higher or equal to said TV, then the condition is considered as being normal (healthy)—step 108. As indicated above, the diagnostic meaning of the measured values for $$\frac{\Delta R}{R} \cdot \alpha \cdot HR \cdot k_{HR}$$

larger than the certain value (e.g. 12) is treated by a physician as those equal to 12.

The following are the experimental results for 60 patients. Table 1 below illustrates the measurement and calculation results for such parameters as heart rate (HR), cardiac index (CI), and Granov-Goor Index (GGI) and Ejection Factor (EF) which characterize the left ventricular condition according to different models. The GGI model is described above, namely is based on a relation between GGI and the product $(HR \cdot k_{HR} \cdot \Delta R/R \cdot \alpha)$; and the EF model is the conventional one based on the interpretation of echo measurements. In this connection, it should be noted that the results of the EF model are relatively subjective as being highly dependent on the physician's interpretation of the measurement results, while the GGF model provides a clear and objective result. The heart rate can be obtained from the ECG measurement or from the impedance wave. As for the cardiac index CI it can be derived from the measured cardiac output $\Delta R/R$ as $CI=(\Delta R/R)/BSA$, where BSA is the body surface area.

TABLE 1

| Patient No | Sex | Age | CI lit/min/m² | GGI | HR | EF % |
|---|---|---|---|---|---|---|
| 1 | F | 57 | 3.5 | 11 | 75 | 55 |
| 2 | M | 59 | 3.1 | 11 | 76 | 60 |
| 3 | M | 44 | 6 | 18 | 89 | 71 |
| 4 | M | 54 | 4.3 | 15 | 75 | 66 |
| 5 | M | 45 | 4.2 | 14 | 69 | 60 |
| 6 | F | 50 | 2.7 | 11 | 52 | 60 |
| 7 | M | 55 | 3.4 | 10 | 81 | 60 |
| 8 | M | 78 | 3 | 9.1 | 80 | 50 |
| 9 | M | 71 | 3.4 | 12 | 59 | 70 |
| 10 | F | 72 | 2.6 | 8.3 | 66 | 37 |
| 11 | F | 53 | 2.3 | 7.9 | 61 | 55* |
| 12 | F | 64 | 2.9 | 16 | 62 | 50 |
| 13 | M | 61 | 2.3 | 6.1 | 57 | 40 |
| 14 | M | 61 | 3.1 | 11 | 60 | 55 |
| 15 | M | 71 | 2.4 | 10 | 53 | 60 |
| 16 | F | 65 | 3.4 | 11 | 70 | 55 |
| 17 | F | 58 | 4.5 | 13 | 62 | 70 |
| 18 | M | 49 | 2.9 | 10 | 56 | 50 |
| 19 | M | 67 | 3.2 | 13 | 55 | 55 |
| 20 | M | 46 | 3.1 | 10 | 62 | 55 |
| 21 | M | 60 | 2.4 | 7.2 | 66 | 38 |
| 22 | M | 57 | 3.9 | 12 | 74 | 63 |
| 23 | F | 57 | 4.5 | 14 | 66 | 74 |
| 24 | F | 62 | 3 | 10 | 67 | 58 |
| 25 | M | 64 | 3.6 | 12 | 63 | 63 |
| 26 | M | 59 | 3.7 | 13 | 70 | 63 |
| 27 | F | 64 | 2.4 | 7.4 | 74 | 36 |
| 28 | F | 70 | 2.6 | 9.8 | 59 | 53 |
| 29 | F | 71 | 3.3 | 12 | 90 | 57 |
| 30 | M | 74 | 3.7 | 12 | 86 | 58 |
| 31 | M | 54 | 2.3 | 4.3 | 112 | 20 |
| 32 | F | 46 | 3.6 | 14 | 70 | 55 |
| 33 | M | 43 | 5.1 | 14 | 89 | 55 |
| 34 | M | 47 | 3.8 | 12 | 67 | 57 |
| 35 | M | 53 | 3.6 | 15 | 55 | 55 |
| 36 | M | 66 | 2.4 | 8.4 | 50 | 36 |
| 37 | M | 43 | 4.1 | 12 | 78 | 60 |
| 38 | M | 48 | 3.8 | 12 | 79 | 55 |
| 39 | F | 51 | 3.4 | 10 | 76 | 65 |
| 40 | F | 62 | 4.1 | 14 | 76 | 56 |
| 41 | F | 51 | 4.5 | 15 | 70 | 60 |
| 42 | M | 72 | 4.3 | 12.7 | 86 | 55 |
| 43 | M | 47 | 3 | 10.6 | 58 | 55 |
| 44 | F | 51 | 3.6 | 11.9 | 60 | 60 |
| 45 | F | 65 | 3.4 | 10.2 | 67 | 60 |
| 46 | F | 82 | 4.2 | 12.2 | 76 | 65 |
| 47 | M | 50 | 4.3 | 14.9 | 67 | 56 |
| 48 | M | 81 | 3.1 | 11.4 | 63 | 55 |
| 49 | M | 58 | 2.4 | 7.6 | 61 | 50 |
| 50 | M | 49 | 4.4 | 13.4 | 88 | 60 |
| 51 | M | 76 | 2.4 | 8 | 63 | 50 |
| 52 | M | 54 | 3.1 | 9.6 | 75 | 53 |
| 53 | M | 55 | 3.4 | 11.4 | 61 | 60 |
| 54 | M | 62 | 5.8 | 14.9 | 93 | 65 |
| 55 | M | 48 | 6.1 | 16.9 | 86 | 60 |
| 56 | M | 60 | 3.4 | 11.1 | 69 | 56 |
| 57 | F | 76 | 3.1 | 12.1 | 59 | 60 |
| 58 | M | 58 | 3.4 | 13.5 | 55 | 59 |
| 59 | M | 53 | 3.6 | 11.1 | 79 | 57 |
| 60 | M | 45 | 4.8 | 12.8 | 89 | 56 |

As can be seen from the above experimental results, the invented GGI model provides for better sensitivity, specificity, and positive and negative predictive values, as compared to the EF model. This is summarized in Table 2 below.

TABLE 2

|  | Granov-Goor Index | Cardiac Index |
|---|---|---|
| Sensitivity | 92.31% | 61.54% |
| Specificity | 100.00% | 97.87% |
| Positive Predictive Value | 100.00% | 88.89% |

TABLE 2-continued

|  | Granov-Goor Index | Cardiac Index |
|---|---|---|
| Negative Predictive Value | 97.92% | 90.20% |

The invention claimed is:

1. A method for use in determining a patient's heart condition, the method comprising:
providing first data indicative of the patient's heart rate and second data indicative of bioimpedance peak value during a cardiac cycle,
wherein said first and second data are characterized by at least one of the following:
(a) said first data comprises a product of the patient's heart rate value and a coefficient $k_{HR}$ which is specific for a patient and which is a correction coefficient for correction of the heart rate; and
(b) said second data comprises a product of a normalized systolic impedance variation, $\Delta R/R$, and a systolic peak time, $\alpha$;
determining a relation between a product of said first and said second data and a certain predetermined value, said relation being indicative of the patient's left ventricular condition enabling to identify left ventricular dysfunction.

2. The method according to claim 1, wherein said relation indicative of the patient's left ventricular dysfunction is determined such that said product of said first and said second data being less than said certain predetermined value corresponds to a condition of the patient's left ventricular dysfunction.

3. The method according to claim 1, wherein said first data indicative of the patient's heart rate comprises a patient's heart rate value.

4. The method according to claim 1, wherein the correction coefficient $k_{HR}$ is equal to 1 when the measured patient's heart rate $HR_{meas}$ within a certain range of normal values between a bottom limit BL and a top limit TL, is equal to $BL/HR_{meas}$ when the measured patient's heart rate $HR_{meas}$ is less than the bottom limit BL of the normal range, and is equal to $TL/HR_{meas}$ when the heart rate $HR_{meas}$ higher than the top limit TL of the normal range.

5. The method according to claim 4, wherein the correction coefficient $k_{HR}$ is equal to 1 when the measured patient's heart rate $HR_{meas}$ is within a range of 60-90, and is equal to $60/HR_{meas}$ when the measured heart rate $HR_{meas}$ is less than 60, and is equal to $90/HR_{meas}$ when the measured heart rate $HR_{meas}$ higher than 90.

6. The method according to claim 5, wherein said second data indicative of electrical bioimpedance changes during a cardiac cycle comprises a product of a normalized systolic peak value impedance, $\Delta R/R$, and a systolic peak time, $\alpha$.

7. The method according to claim 6, wherein said certain predetermined value is equal to 10.

8. The method according to claim 4, wherein said second data indicative of electrical bioimpedance changes during a cardiac cycle comprises a product of a normalized systolic impedance variation, $\Delta R/R$, and a systolic peak time, $\alpha$.

9. A system for use in determining a patient's heart condition, the system comprising:
a data input utility for receiving first data indicative of the patient's heart rate and receiving second data indicative of bioimpedance variations during a cardiac cycle,
wherein said first and second data are characterized by at least one of the following:
(a) said first data comprises a product of the patient's heart rate value and a coefficient $k_{HR}$ which is specific for a patient and which is a correction coefficient for correction of the heart rate; and
(b) said second data comprises a product of a normalized systolic impedance variation, $\Delta R/R$, and a systolic peak time, $\alpha$;
a data processing and analyzing utility configured for determining a product of said first and said second data, determining a relation between said product and a certain predetermined value, and based on said relation generating data indicative of the patient's left ventricular condition; and
a data output utility for exposing to user data indicative of the patient's left ventricular condition.

10. The system according to claim 9, wherein said data input utility is responsive to user entered data comprising at least one of said first and second data.

11. The system according to claim 10, wherein said data input utility is responsive to output data of a measurement device, said output data comprising at least one of said first and second data.

12. The system according to claim 9, wherein said data input utility is responsive to output data of a measurement device, said output data comprising at least one of said first and second data.

13. The system according to claim 9, wherein said data processing and analyzing utility operates to determine whether said product of said first and said second data is less than said certain predetermined value and generating data indicative the condition of the patient's left ventricular dysfunction.

14. The system according to claim 9, wherein said first data indicative of the patient's heart rate comprises a patient's heart rate value.

15. The system according to claim 9, wherein the correction coefficient $k_{HR}$ is equal to 1 when the measured patient's heart rate $HR_{meas}$ within a certain range of normal values between a bottom limit BL and a top limit TL, is equal to $BL/HR_{meas}$ when the measured patient's heart rate $HR_{meas}$ is less than the bottom limit BL of the normal range, and is equal to $TL/HR_{meas}$ when the heart rate $HR_{meas}$ is higher than the top limit TL of the normal range.

16. The system according to claim 15, wherein the correction coefficient $k_{HR}$ is equal to 1 when the measured patient's heart rate $HR_{meas}$ within a range of 60-90, and is equal to $60/HR_{meas}$ when the measured heart rate $HR_{meas}$ less than 60, and is equal to $90/HR_{meas}$ when the measured heart rate $HR_{meas}$ higher than 90.

17. The system according to claim 16, wherein said second data indicative of electrical bioimpedance changes during a cardiac cycle comprises a product of a normalized impedance variation, $\Delta R/R$, and a systolic peak time, $\alpha$.

18. The system according to claim 15, wherein said second data indicative of electrical bioimpedance changes during a cardiac cycle comprises a product of a normalized systolic impedance variation, $\Delta R/R$, and a systolic peak time, $\alpha$.

19. The system according to claim 18, wherein said certain predetermined value is equal to 10.

* * * * *